United States Patent [19]

Rigdon

[11] 4,219,892

[45] Sep. 2, 1980

[54] KNEE BRACE FOR PREVENTING INJURY FROM LATERAL IMPACT

[76] Inventor: Robert W. Rigdon, 6318 142nd St. SW., Edmonds, Wash. 98020

[21] Appl. No.: 9,528

[22] Filed: Feb. 5, 1979

[51] Int. Cl.$^2$ ............................................. A41D 13/06
[52] U.S. Cl. ......................................... 2/24; 128/80 C; 128/DIG. 20
[58] Field of Search ............................ 2/24, 22, 16, 2; 128/80 C, DIG. 20, 165

[56] References Cited

U.S. PATENT DOCUMENTS

| | | | |
|---|---|---|---|
| 1,258,052 | 3/1918 | Stall | 128/165 |
| 3,551,912 | 1/1971 | Viglione | 2/24 |
| 3,677,265 | 7/1972 | Brabazon | 2/24 |
| 3,799,159 | 3/1974 | Scott | 128/80 C |
| 3,945,047 | 3/1976 | Jarrell, Jr. | 2/24 |
| 4,142,252 | 3/1979 | Storer | 2/24 |

*Primary Examiner*—H. Hampton Hunter

*Attorney, Agent, or Firm*—Robert K. Stoddard; C. Michael Zimmerman

[57] ABSTRACT

A pair of cuffs are positioned on the thigh and calf respectively adjacent the knee joint. Each of these cuffs encloses and is backed by a fluid-filled chamber made of a flexible resilient material. The inner surface of this chamber is bonded to an elasticized fabric band which encircles the leg and positions each of the cuffs immediately adjacent the knee joint.

An accordion-folded section of tubing extends from the upper to the lower fluid filled chamber along each side of the knee forming a unitary fluid-filled system. A pair of flexible but inextensible straps overlays each of the accordion-folded tubes and is securely fastened to the cuffs. Upon lateral impact, fluid migrates from the side of the knee which has been struck to the opposite side causing the cuffs to firmly grip the thigh and calf, and the accordion-folded tube on the opposite side to fill with fluid, creating compressive force between the knee joint and the tensioned straps and preventing dislocation of the knee joint.

11 Claims, 3 Drawing Figures

U.S. Patent  Sep. 2, 1980  Sheet 1 of 2  4,219,892
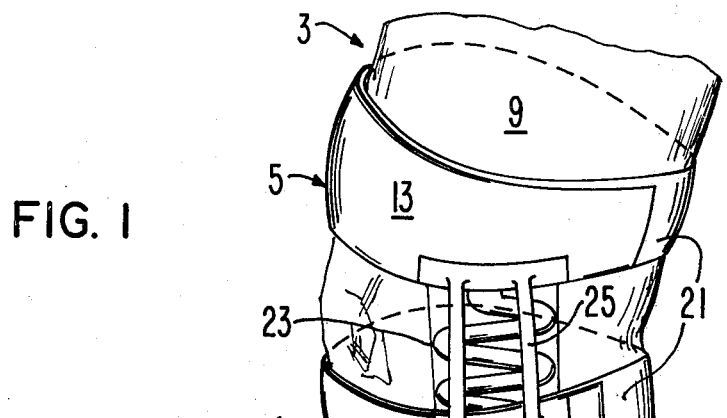
FIG. 1
FIG. 2
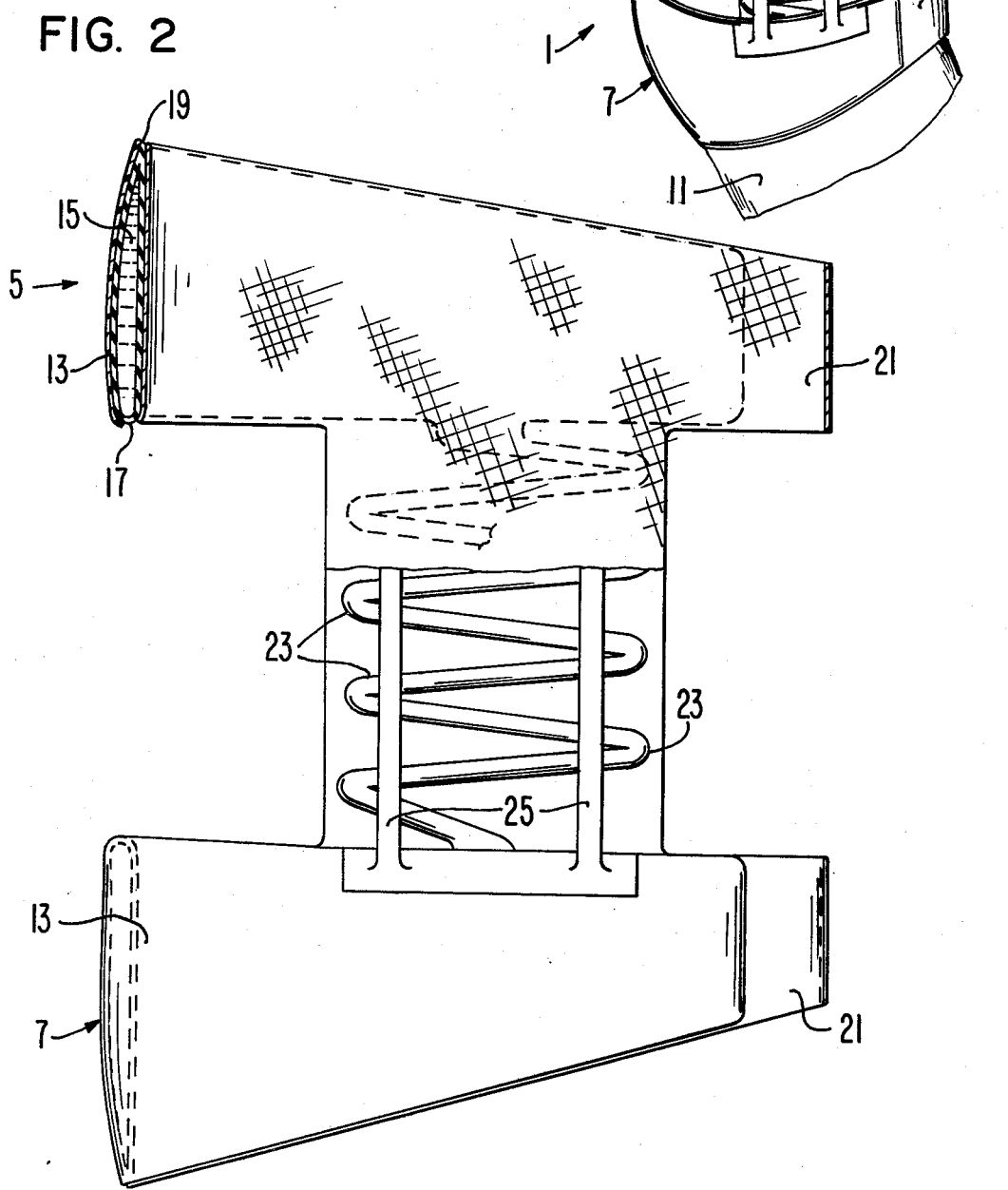

KNEE BRACE FOR PREVENTING INJURY FROM LATERAL IMPACT

BACKGROUND OF THE INVENTION

The invention relates generally to the field of prevention of athletically induced injury to human joint structures, and more particularly to means for preventing injuries to the human knee in heavy contact athletic activities such as football.

A wide variety of protective devices has come into being in order to minimize injuries to athletes in heavy contact sports such as football. Various face guards, helmets and shoulder pads have proven more or less effective in minimizing or eliminating many of the injuries produced by crushing impact on various structures of the human body.

However, adequate protection of joints and especially the knee joint in such sporting activities remains a more-or-less unsolved problem. Dislocation or actual fracturing of the bone structures of the joints, tearing of ligaments and damage to associated muscles have proven difficult to prevent because of the necessity to preserve full unhindered movement of the joint. For example, knees could be adequately protected against injury by a structure resembling a cast which completely immobilized the joint. However, no athlete could possibly use such a device in any sport which required speed, flexibility and agility. Consequently there continues to be a need for a brace or support structure which is lightweight and flexible, involves little or no risk of injury either to the player wearing it or to others who may come in contact with him, and is easy to position correctly and keep in place in use.

Such a knee brace must permit free movement of the knee as in running, jumping, stooping, and must also permit slight rotatory movement of the human calf with respect to the thigh, as would be involved in rapid changes of direction in "broken field running". These movements must moreover be permitted without excessive weight, discomfort, blockage of normal blood circulation or hindrance of normal heat rejection from the region of the knee.

The most serious type of injury with which such a knee brace must cope is the sort that results when a football player, for example, receives a lateral blow to the knee or the adjacent regions of thigh or calf while the leg is fully extended or nearly so. The ability of the human knee to flex laterally or successfully resist high lateral forces is very limited and the consequent damage can be very severe. Accordingly, any adequate knee support or brace must have a considerable ability to reinforce the knee against lateral-impact-produced injury.

DESCRIPTION OF THE PRIOR ART

U.S. Pat. No. 3,551,912 issued Jan. 5, 1971 to Joseph P. Viglione illustrates and claims a knee brace consisting essentially of a flat fluid-filled sheet which when wrapped about the knee forms a fluid-cushioned protective sleeve surrounding the knee. While such a device provides some protection against crushing impact upon the structures of the knee, it does very little to prevent the dislocative injuries which result from heavy lateral impact on the knee. That is, the invention of this patent does little to prevent a lateral "breaking open" of the knee joint, since it lacks any sort of bracing structure and relies solely on cushioning. Furthermore, the invention of U.S. Pat. No. 3,551,912, by surrounding the knee with a broad unbroken, double-walled fluid-filled sheet unnecessarily restricts normal flexure of the knee.

U.S. Pat. No. 3,945,047 issued to Richard P. Jarrell, Jr., on Mar. 23, 1976 details a knee protective device which, unlike the immediately preceding prior art, does provide additional stiffening of the knee joint against lateral impact. In the Jarrell patent, the knee is reinforced along both sides by a joint structure made up of a series of metallic discs and pivot pins. The joint structures are enclosed within a fluid-filled sac or cushion extending at either side of the knee joint such that no part of the metallic joint structure is exposed. While the invention of this prior art patent does provide reinforcement to the knee joint against lateral impact, it does so at the expense of flexibility of the knee, increase in weight, and interference with normal cooling of the knee region. The fluid-filled sacs or cushions extending along either side of the knee and enclosing the reinforcing joint structure must inevitably add to the resistance to flexure of the knee joint as well as hindering normal cooling through evaporation of perspiration.

SUMMARY OF THE INVENTION

The principal object of the present invention is to provide a joint support structure which adequately braces the joint against injury due to lateral impact.

A second object of the present invention is to provide such a structure for the human knee joint which functions without hindering flexure of the knee.

A third object of the present invention is to provide a knee brace which is relatively lightweight and comfortable to wear.

To the above ends, the knee brace according to the present invention comprises a pair of cuff members each of which comprises an outer non-stretchable but flexible shell, which encloses and is lined by a fluid-filled chamber which readily conforms to the shape of the user's leg and securely grips the leg. One of these cuffs is positioned on the upper calf while the other is positioned on the lower thigh, both immediately adjacent the knee, each being held in place by an inner band of elasticized fabric. Along each side of the knee an accordion-folded length of flexible tubing extends from the upper cuff to the lower cuff, interconnecting the fluid-filled chambers to form a unitary fluid-filled system. Flexible but inextensible members interconnect the pair of cuffs and extend along either side of the knee, overlaying the accordion-folded tubes.

Upon lateral impact to the knee, fluid is caused to migrate from the struck side of the knee to the opposite side causing expansion of the fluid-filled chamber and accordion-folded tube on the opposite side. The expansion of the fluid-filled chamber on the opposite side of the knee increases the pressure along that side preventing shifting of the cuff along the thigh and calf. The swelling or expansion of the accordion-folded flexible tube along the opposite side creates compressive force between the knee and the overlying inextensible strap members. The result is that the knee is braced along the side opposite the point of impact, thereby preventing injurious opening of the knee on that side.

These and other features, objects and advantages of the present invention together with the best means contemplated by the inventor for carrying out the invention will become more apparent from reading the following more detailed description of a preferred embodiment and perusing the drawing in which:

BRIEF DESCRIPTION OF THE DRAWING

FIG. 1 is a perspective view illustrating the use of the knee brace according to the present invention and its positioning relative to the human knee and leg;

FIG. 2 is a view partly in elevation and partly in section showing the details of the structure of the knee brace according to the present invention;

DETAILED DESCRIPTION OF A PREFERRED EMBODIMENT

Figure 3:
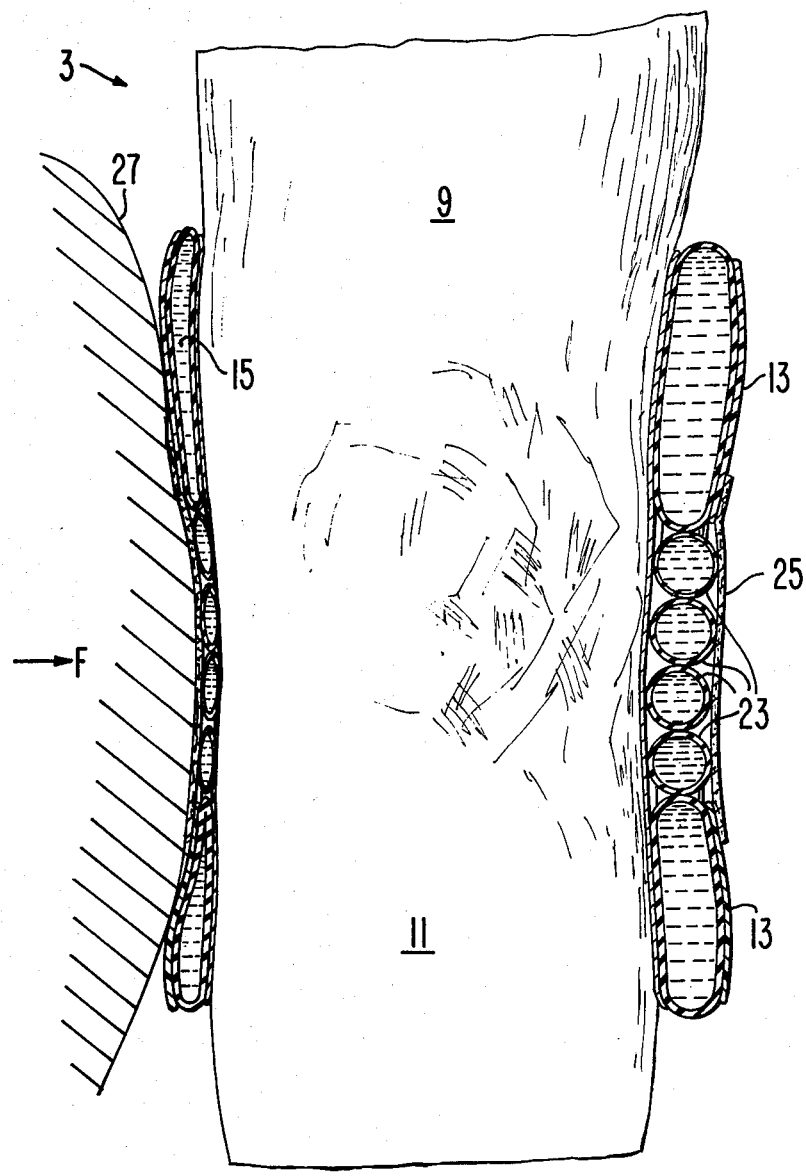
FIG. 3 is a lateral cross-sectional view of the knee brace according to the present invention illustrating the effect of a lateral impact to the region of the knee.

In FIG. 1 is shown the knee brace 1 of the present invention in place on the leg 3 of a user. Brace 1 consists fundamentally of an upper cuff 5 which encircles and grips the lower region of the thigh 9 of leg 3, and a lower cuff 7 which similarly encircles the upper portion of the calf 11 of leg 3. Cuffs 5 and 7 can thus be thought of as means to circumferentially, frictionally engage a pair of jointed limbs over a region thereof adjacent the joint.

The detailed view of FIG. 2 shows upper cuff 5 partially cut away revealing the inner structure thereof while lower cuff 7 is shown in elevation. It should be noted that cuffs 5 and 7 are identical in structure with the exception of minor variations in shape and dimension to adapt them to adequately fit the thigh 9 and calf 11 of the user.

As shown in FIG. 2, cuffs 5 and 7 consist of an outer shell 13 which can be suitably molded or otherwise fabricated from a strong resilient but flexible plastic material such as a polypropylene plastic. Each of shells 13 is curved in an outwardly convex fashion to provide a concave inner surface within which is located a fluid-filled chamber 15, one of which is clearly shown in sectional view in upper cuff 5 in FIG. 2. Chamber 15 may be formed by simply molding a flexible, durable plastic material to the appropriate shape or it may instead be formed out of a thin flexible plastic sheet folded along a lower edge 17 and joined together along an upper edge 19 by thermal or cement bonding. A fluid-filled chamber 15 is joined to the inner surface of each of shells 13 by any suitable known means of adhesive bonding along the inner concave surface of these shells.

Any non-toxic, non-corrosive fluid may be used within chambers 15. The principal criteria for its selection would be its compatibility with the materials with which it is in contact, its viscosity, weight, and vapor pressure. In practice, water may be used alone, or with additives.

There are several alternative choices for the structure of cuffs 5 and 7. When desired, outer shells 13 may themselves form the outer wall of chambers 15 by joining a single layer of flexible plastic, at its edges only, to the inner side of each shell 13. Alternatively, by selecting the material from which to form chamber 15 to have sufficient strength and resistance to stretching, it is possible to provide that the outer walls of chambers 15 serve the same functions as the shells 13.

In order to insure that each of cuffs 5 and 7 can be readily positioned and maintained in place immediately above and below the knee joint of the user and also for the sake of comfort, a broad band 21 of a resiliently stretchable fabric, which could be an elasticized nylon, forms the innermost surface of cuffs 5 and 7. Fabric band 21 may be adhesively bonded to the inner surface of fluid-filled chamber 15 by any suitable means.

An accordion-folded or serpentine tube 23 extends between upper and lower fluid-filled chambers 15 and provides fluid communication between these chambers, thus forming a unitary fluid-filled system. Tubing 23 may be employed only on the side of brace 1 which will be adjacent the inner side surface of the knee in use, or a tube 23 may be provided at both the inside and outside of the knee. Tube 23 may be joined at either of its ends for fluid communication between chambers 15 by means of a molded plastic union (not shown) which may be cemented to chambers 15 and the ends of tube 23, or alternatively, tube 23 and chambers 15 may be formed as one piece. In the latter case, of course, no actual folding of tube 23 need be involved since the serpentine shape can be produced in the mold. Similarly, tube 23 can be molded in serpentine shape as a separate piece and joined to chambers 15 by thermal or cement bonding.

Upper cuff 5 and lower cuff 7 are joined by flexible but inextensible members 25, a pair of which are illustrated in FIGS. 1 and 2. Also members 25 could be used singly or in any number depending upon their width and tensile strength. Members 25 are joined at their upper and lower ends to shells 13 by any known means of fastening such as clamping, cement bonding, etc., and may be formed of any flexible material having high tensile strength such as heavy canvas, glass or wire cloth, or other similar materials. Alternatively, members 25 may be formed of the same material as shells 13 and may then comprise an integral part of these shells. Members 25 freely permit the sort of relative motion of cuffs 5 and 7 that would be required in the normal action of a knee joint in running, for example, but strictly prevent any increase in the distance separating the upper and lower cuffs 5 and 7.

FIG. 3 illustrates the effect of knee brace 1 in protecting the human knee against lateral impact. In FIG. 3 a relatively large force F is applied to the leg 3 of the wearer by an impinging object 27 which could, for example, be the shoulder of an attacking football player. Under the influence of the lateral force produced by impinging object 27 against all portions of the unitary fluid flow system on the left side of the knee in FIG. 3, fluid will flow to the right, essentially overfilling the portions of chambers 15 and the tubing 23 on the right side of the knee. Such overfilling, of course, generates considerable pressure along the right side of the knee.

The effect of this pressure is two-fold: upper cuff 5 and lower cuff 7 momentarily exert a powerful grip on both the thigh 9 and calf 11 of leg 3 such that movement of these cuffs is resisted. Simultaneously, the walls of tube 23, being thin and resilient are caused to expand, creating compressive force between the right side of the knee in FIG. 3 and the adjacent inextensible member 25, which is held in tension. Consequently, the members 25, fixedly located at their ends by firmly-gripping cuffs 5 and 7, together with the compressively loaded tubing 23, form a truss or brace which strongly reinforces the internal structure of the knee and prevents the severe injury which would result from the opening of the knee to the right in FIG. 3 under the influence of the force F of impinging object 27.

When object 27 is removed, the fluid within chamber 15 and tubes 23 will redistribute itself in a more or less uniform pattern by the natural process of equalization of pressure within the fluid. In normal use, therefore, tubes 23 are relaxed and do not exert compressive force between members 25 and the adjacent surface of the knee, permitting free flexure of the knee joint as needed in running. Such flexure is particularly promoted by the accordion-folded configuration of tube 23 and by the flexibility of strap members 25.

It should be noted that the degree of the bracing or trussing effect of knee brace 1 can be selected through design and dimensioning of the accordion-folded tubing 23 and its expansive compliance (ratio of cross-sectional increase to pressure increase) relative to that of the fluid-filled chambers 15. The important criterion in such dimensioning and design is that under the influence of a lateral blow, tube 23 must expand sufficiently to exert an adequate protective counterbalancing force on the knee at the side opposite the point of application of the blow.

It may further be noted that in cases where it is only necessary to protect the knees against lateral impact against the outer side surface of the knee, tubing 23 and member 25 need to be provided only on the inside of the knee. However, where lateral blows may be expected against either the inner or outer side of the knee, such tubing 23 and member 25 must be provided on each side of the knee.

Although the invention has been described with some particularity in reference to a single embodiment which comprises the best means known by the inventor of carrying out his invention, it will be obvious to the skilled worker in the art that many modifications can be made and many apparently different embodiments derived without departing from the scope of the invention. Therefore, it is intended that the scope of the invention be interpreted only from the following claims.

I claim:

1. A device for preventing accidental dislocation of the joint between a pair of limbs of the human body as a result of a blow to said joint or limbs, comprising: a first means to circumferentially frictionally engage a first one of said limbs about a region thereof adjacent said joint, a second means to circumferentially frictionally engage the other of said limbs about a region thereof adjacent said joint, a flexible substantially inextensible member extending from said first means to said second means across said joint, said flexible inextensible member being connected to each of said means to engage and, interposed between said flexible inextensible member and said joint, a first means responsive to the force of impact of a blow to the region of said joint generally on the side opposite said flexible inextensible member, to expand and create compressive force between said joint and said flexible inextensible member, to contract upon subsidence of said force of impact and to thereby brace said joint against movement under the influence of said blow, said means responsive to said force of impact and said flexible member permitting unhindered flexure of said joint in the absence of said blow.

2. The device of claim 1 wherein said joint is a human knee joint and said first one of said limbs is the thigh and said other one of said limbs is the calf.

3. The device of claim 1 wherein each of said means to frictionally engage said limbs further includes second means responsive to said force of impact to: increase the frictional force between each of said means to frictionally engage, and the corresponding one of said limbs; and to decrease said frictional force in response to subsidence of said force of impact.

4. The device of claim 1 wherein each of said means to engage comprises an outer shell shaped and dimensioned to be receivable circumferentially about a corresponding one of said limbs.

5. The device of claim 4 further including a compliant fluid-filled chamber within each of said outer shells, each of said fluid-filled chambers extending circumferentially between said one of said limbs and said shell.

6. The device of claim 5 wherein said fluid-filled chambers are mutually interconnected for fluid flow therebetween.

7. The device of claim 6 wherein a flexible tube mutually interconnects said fluid-filled chambers.

8. The device of claim 7 wherein said joint is a human knee joint and said flexible tube is serpentine in shape and is so joined to said fluid filled chambers as to lie along a side of said knee joint when said shells are in position on said limbs.

9. The device of claim 7 wherein said first means responsive to the force of impact of said blow comprises said flexible tube extending in fluid communication between said fluid-filled chambers.

10. The device of claim 1 wherein said flexible, substantially inextensible member extending between said first and second means to circumferentially frictionally engage said limbs comprises a strap.

11. The device of claim 3 wherein said first and second means responsive to said force of impact comprise a unitary fluid-filled system extending: circumferentially of said limbs within said first and second means to engage said limbs, and between said flexible member and said joint.

* * * * *